(12) United States Patent
Roesler et al.

(10) Patent No.: US 6,458,293 B1
(45) Date of Patent: Oct. 1, 2002

(54) POLYUREA COATINGS FROM DIMETHYL-SUBSTITUTED POLYASPARTIC ESTER MIXTURES

(75) Inventors: Richard R. Roesler, Wexford; Edward P. Squiller, Pittsburgh, both of PA (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/363,174

(22) Filed: Jul. 29, 1999

(51) Int. Cl.[7] .................................................. C09K 3/00
(52) U.S. Cl. .................................................. 252/182.23
(58) Field of Search ....................... 528/288; 252/182.23

(56) References Cited

U.S. PATENT DOCUMENTS

| | | | |
|---|---|---|---|
| 5,126,170 A | 6/1992 | Zwiener et al. | 427/385.5 |
| 6,169,141 B1 * | 1/2001 | Kurek et al. | 524/589 |

* cited by examiner

Primary Examiner—Cephia D. Toomer
(74) Attorney, Agent, or Firm—Joseph C. Gil; Thomas W. Roy

(57) ABSTRACT

A method for making a polyurea coating by: (a) coating a substrate with a coating composition containing effective coating-forming amounts of (i) a polyisocyanate component, and (ii) an polyaspartic ester mixture. The invention also relates to the coatings made by the method, the polyaspartic ester mixtures used to make the coatings, and methods to make the mixtures.

26 Claims, No Drawings

POLYUREA COATINGS FROM DIMETHYL-SUBSTITUTED POLYASPARTIC ESTER MIXTURES

FIELD OF THE INVENTION

The invention relates to the field of polyaspartic ester mixtures, and more particularly to the use of polyaspartic ester mixtures in polyurea coating applications.

BACKGROUND OF THE INVENTION

Two-component polyurea coating compositions containing a polyisocyanate in combination with a polyaspartic ester component are known. They are suitable for the formation of coatings and can be adjusted to produce coatings that are hard, elastic, abrasion resistant, solvent resistant, and especially weather resistant. Despite their wide-spread use, however, known coating compositions contain disadvantages which limit their use in important applications.

Coating compositions with an appreciable amount of polyaspartic esters with dimethyl groups would be desired because dimethyl groups would add desired properties to coatings made from such compositions. U.S. Pat. No. 5,126,170 discloses a process for making polyurethane coatings in which an isocyanate-reactive component b) includes a polyaspartic ester mixture made from an optionally-substituted maleic or fumaric acid ester and a primary amine. Although the patent teaches that maleic acid or fumaric acid ester can be substituted with dimethyl, diethyl and di-n-butyl esters, it has been observed that during the Michael Addition Reaction of dimethyl maleate and primary amines, dimethyl maleate isomerizes to dimethyl fumarate in the presence of amines, according to the following geometric isomerization reaction:

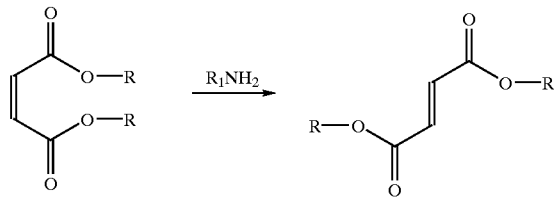

The dimethyl fumarate forms long needle-like crystals which no longer participate in the Michael Addition Reaction and prevent the reaction from completing. Although the resulting reaction produces yields of only about 30 to 40%, the entire composition is useless for commercial purposes. This is because the composition contains a mixture of compounds that preclude the formation of a suitable coating. The crude mixture generally contains (i) dimethyl fumarate crystals, (ii) starting diamine material, (iii) mono-primary-amine-monoaspartate and (iv) diaspartate. The presence of crystals in such a mixture prevents the formation of a coating. Filtering the crystals from the mixture has not been an option because filtration removes an appreciable amount of starting material, thereby adding substantial costs. Also, a filtrated mixture contains unreacted primary amines whose presence undesirably speed the crosslinking reaction.

U.S. Pat. No. 5,126,170 teaches preparing its polyaspartic esters in a solvent. The use of a 50% methanol reaction medium, however, is not practical in a production situation for the following reasons. First, the use of a 50% solution means that yields of product are half of what could be achieved if the reaction was run without solvent. Second, the methanol is highly flammable and its presence in manufacturing would be a safety hazard. Finally, in order for the polyaspartic ester to be used with polyisocyanates, the methanol would have to be completely removed. Even small, residual amounts of methanol would react with polyisocyanates to form urethanes, which would decrease the crosslink density of the films and so cause a decrease in properties.

For the foregoing reasons, it has been desired to develop a method for making a polyurea coating ingredient that contains an appreciable amount of dimethyl-substituted polyaspartic esters.

SUMMARY OF THE INVENTION

The invention relates to a method for making an asymmetric polyaspartic ester mixture by sequentially (a) forming an ester mixture containing a dimethyl-substituted first ester component and a second ester component substituted with an alkyl group having at least two carbon atoms and (b) reacting the ester component with an amine component, such that the equivalent number ratio of the first ester component and the second ester component is sufficient to prevent the formation of a reaction-stopping crude mixture containing dimethyl fumarate crystals.

The invention also relates to a polyurea coating composition containing a polyisocyanate component, the ester component used to make the polyaspartic ester mixture, and the asymmetric polyaspartic ester mixture, a method for making a coating with the polyaspartic ester mixture, and a coating made with the asymmetric polyaspartic ester mixture. These and other features, aspects, and advantages of the present invention will become better understood with reference to the following description and appended claims.

DESCRIPTION OF THE INVENTION

As used in this application, the term "cyclic amine" refers to amines which have at least one primary amine group attached to a cyclic (closed ring) group, e.g., an amine attached to a secondary ring carbon. The term "acyclic amine" refers to an amine that does not have a primary amine group attached to a cyclic, closed end group.

The invention is based on the surprising discovery that the crystallization that has been observed during the reaction of dimethyl-substituted maleic acid or dimethyl-substituted fumaric acid and a primary amine can be substantially reduced or eliminated altogether by reacting the amine with a mixture containing dimethyl maleate and a small amount of at least one dialkyl maleate having two or more carbon atoms, e.g., diethyl maleate, dipropyl maleate. By practicing the invention, polyaspartic esters based on dimethyl maleate can now be made simply and directly, without crystallization and without the need for solvents. The asymmetric polyaspartic ester mixtures produced can then be used as isocyanate-reactive components in coating compositions for making polyurea coatings having a novel structure and improved properties.

Maleic acid esters and fumaric acid esters include suitable dialkyl maleates or dialkyl fumarates. Suitable dialkyl maleates include dimethyl maleate, diethyl maleate, dipropyl maleate, dibutyl maleate, methyl propyl maleate, ethyl propyl maleate, and the like. Suitable dialkyl fumurates include dimethyl fumarate, diethyl fumarate, dipropyl fumarate, dibutyl fumarate, methyl propyl fumarate, ethyl propyl fumarate, and the like.

The amine component is generally selected from difunctional or trifunctional cyclic and acylic amines which can accomplish the objects of the invention. Suitable amines can be selected from the following. Suitable acyclic difunctional amines include but are not limited to ethylene diamine, 1,2-diaminopropane, 1,4-diaminobutane, 1,6- diaminohexane, 2,5-dimethylhexane, 2,2,4- and/or 2,4,4-trimethyl-1,6-diaminohexane, 1,11-diaminoundecane, 1,12-diaminododecane, 1-amino-3,3,5-trimethyl-5-aminomethylcyclohexane, 2,4- and/or 2,6-hexahydrotolylenediamine, 2,4'- and/or 4,4'-diaminodicyclohexylmethane, and 3,3'-dimethyl-4,4'-diaminodicyclohexylmethane. Suitable cyclic amines include aromatic polyamines such as 2,4- and/or 2,6-diaminotoluene, and 2,4'- and/or 4,4'-diaminodi-phenyl-methane are also suitable but less preferred. Other suitable cyclic amines include bis-(3-methyl-4-aminocyclohexyl) methane, 2,4-diamino-1-methyl, cyclohexane, and 2,6-diamino-1-methyl cyclohexane.

Suitable trifunctional amines include 4-aminomethyl-1,8-diamino-octane (also known as triaminononane supplied by Monsanto Company), tris-(2-aminoethyl)amine. It is believed that tetrafunctional amines, e.g., N,N,N',N'-tetrakis-(2-aminoethyl)-1,2-ethanediamine are also suitable.

The equivalent number ratio of (i) the dimethyl maleates (or the dimethyl fumurates) to (ii) the dialkyl maleates (dialkyl fumurates) that have at least 2 carbon atoms is sufficient to prevent the formation of a reaction-stopping crude mixture containing dimethyl fumarate crystals. It has been discovered that cyclic amines containing substituted functional groups adjacent to a cyclically-bound amine group exhibit different behavior than acyclic amines and cyclic amines containing substituted groups that are not adjacent to a cyclically-bound amine group. As such, the following ranges are critical.

When a cyclic amine containing a substituted functional group adjacent to a cyclically-bound amine group is used, the equivalent number ratio is from less than 5:5 to more than 0:10, preferably from about 4.5:5.5 to 1:9, and even more preferably from about 4:6 to about 2:8. Stated in a number percentage basis, the amount of the dimethyl-substituted maleic acid ester or fumaric acid ester is present from less than 50% to more than 0%, preferably from about 45% to about 10%, and even more preferably from about 40 to about 20%, based on the total number of esters. Examples of such amines containing substituted groups adjacent to cyclically-bound amine groups include bis-(3-methyl-4-aminocyclohexyl) methane, 2,4-diamino-1-methyl, cyclohexane, and 2,6-diamino-1-methyl cyclohexane.

When an acyclic amine or a cyclic amine with or without a substituted group that is not adjacent to a cyclically-bound amine group is used, the equivalent number ratio is from less than 9:1 to more than 0:10, preferably from 8.5:1.5 to 1:9, and even more preferably 8:2 to 5.5. Stated in a number percentage basis, the amount of the dimethyl-substituted maleic acid ester or fumaric acid ester is present from less than 90% to more than 0%, preferably from about 85% to about 10%, and even more preferably from about 80 to about 50%, based on the total number of esters. The equivalent number ratio of the amine component to the ester component is generally about 1:1. As such, the ratio of the first ester component and the second ester component must be greater than 0:10. That is, the first ester component must be present in an amount that is greater than 0%, based on the total number of esters in the ester component.

The polyisocyanate component used to react with the polyaspartic ester mixtures includes any polyisocyanate, which, when used in accordance with the invention, meets the object of the invention. Suitable polyisocyanates for use as polyisocyanate component in accordance with the present invention include the known polyisocyanates of polyurethane chemistry. Examples of suitable low molecular weight polyisocyanates having a molecular weight of 168 to 300 include 1,4-diisocyanatobutane, 1,6-hexamethylene diisocyanate, 2,2,4- and/or 2,4,4-trimethyl-1,6-hexamethylene diisocyanate, dodecamethylene diisocyanate, 1,4-diisocyanatocyclohexane, 1-isocyanato-3,3,5-trimethyl-5-isocyana-tomethylcyclohexane (IPDI), 2,4'- and/or 4,4'-diisocyanato-dicyclohexyl methane, 2,4- and/or 4,4'-diisocyanatodiphenyl methane and mixtures of these isomers with their higher homologues which are obtained in a known manner by the phosgenation of aniline/formaldehyde condenses, 2,4- and/or 2,6-diisocyanatotoluene and any mixtures of these compounds. Preferred cyclic is ocyanates include diphenylmethane 4,4'-diisocyanate (MDI), diphenylmethane 2,4'-diisocyanate, 2,4- and/or 2,6-diisocyanatotoluene. Preferred aliphatic isocyanates include hexamethylene diisocyanate, isophorone diisocyanate, 2,4'- and/or 4,4'-diisocyanato-dicyclohexyl methane.

Additional suitable polyisocyanate components include derivatives of the above-mentioned monomeric polyisocyanates, as is conventional in coatings technology. These derivatives include polyisocyanates containing biuret groups as described, for example, in U.S. Pat. Nos. 3,124,605 and 3,201,372 and DE-OS 1,101,394, incorporated herein by reference in their entirety; polyisocyanates containing isocyanurate groups as described in U.S. Pat. No. 3,001,973, DE-PS 1,022,789, 1,222,067 and 1,027,394 and DE-OS 1,929,034 and 2,004,048, incorporated herein by reference in their entirety; polyisocyanates containing urethane groups as described, for instance, in DE-OS 953,012, BE-PS 752,261 and U.S. Pat. Nos. 3,394,164 and 3,644,457; polyisocyanates containing carbodiimide groups as described in DE-PS 1,092,007, U.S. Pat. No. 3,152,162 and DE-OS 2,504,400, 2,537,685 and 2,552,350, incorporated herein by reference in their entirety; and polyisocyanates containing allophanate groups as described, for example, in GB-PS 994,890, BE-PS 761,626 and NL-OS 7,102,524. Suitable polyisocyanates also include polyisocyanates that contain uretdione groups. In one embodiment, asymmetric trimers such as those in U.S. Pat. No. 5,717,091, incorporated herein by reference in its entirety, can be used.

Isocyanate group-containing prepolymers and semi-prepolymers based on polyisocyanates can also be used as the polyisocyanate component. These prepolymers and semi-prepolymers generally have an isocyanate content ranging from about 0.5 to 30% by weight, preferably about 1 to 20% by weight, and are prepared in a known manner by the reaction of starting materials, e.g., isocyanate-reactive compounds such as polyols, at an NCO/OH equivalent number ratio of about 1.05:1 to 10:1, preferably about 1.1:1 to 3:1.

The asymmetric polyaspartic ester mixtures of the invention are made by combining a suitable polyamine component with an ester component containing maleic acid/fumaric acid mixture containing a dimethyl-substituted maleic acid/fumaric acid ester and a maleic acid/fumaric acid ester substituted with an alkyl group containing at least two carbon atoms in suitable amounts under conditions that favor the reaction of the reactants.

The duration of the reaction varies. Reactions involving aliphatic diamines such as hexane-diamine and 2-methyl-1,5-pentanediamine can be fully completed within two weeks. Reactions involving cyclic diamines such as $H_{12}$MDI and 4'-dimethyl $H_{12}$MDI ordinarily take a few months, e.g., 2-3 months, depending on the cyclic amine used when the reaction has reached 97 or 98% completion. Since it can take as long as 52 to 100 weeks for the reaction to reach 100% completion, it is ordinarily not practical to wait for full completion. Specific duration times can be obtained by routine experimentation. The yields at which the polyaspartic esters are produced are generally at least at about 70, 80 and preferably about 100%. The method is ordinarily practiced without any appreciable amount of an organic solvent, e.g., generally less than about 10% preferably less than 5%, based on the total weight of the solution, and even more preferably no solvents.

Generally, when difunctional amines are used, the asymmetric polyaspartic ester mixture includes, in addition to pure compounds, a polyaspartic ester having the formula:

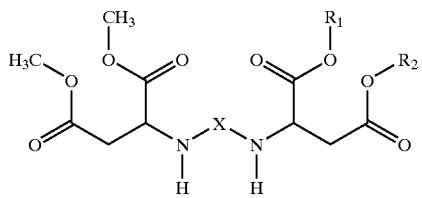

in which X is a hydrocarbon group obtained by the removal of amino groups from a amine corresponding to the formula, $X-(NH_2)_n$ in which $R_1$ and $R_2$ each are the same or different and each is an alkyl group having at least two carbon atoms and n is two. When trifunctional amines are used, the composition includes, in addition to pure compounds, one or both of the following polyaspartic esters:

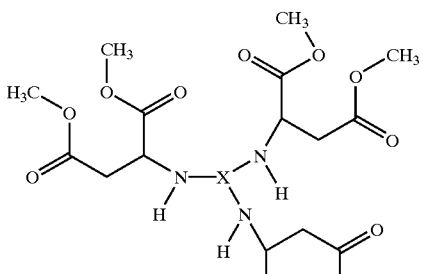

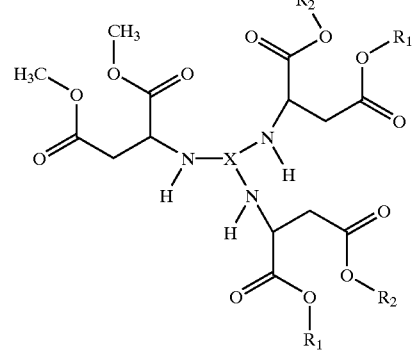

in which X is a hydrocarbon group obtained by the removal of amino groups from an amine corresponding to the formula $X-(NH_2)_n$ in which $R_1$ and $R_2$ each are the same or different and each is an alkyl group having at least two carbon atoms and n is three.

The method provides previously unavailable advantages. Since the method avoids the crystallization that ordinarily forms when dimethyl-substituted esters or maleic or fumaric acid reacts with amines, the method avoids the formation of a commercially useless reaction-stopping crude mixture containing dimethyl fumarate crystals (and other compounds) typically formed by known methods. Also, since the method of the invention does not require the use of solvents, e.g., methanol, it produces polyaspartic ester mixtures in greater yields than solvent-based systems, and avoids the fire hazards typically associated with flammable solvents. Also, since the method does not use solvents such as methanol, the crosslink density and properties of the films are not adversely affected by the polyurethanes which form by the reaction of residual amounts of methanol would react with polyisocyanates to form urethanes.

A polyurea coating composition can readily be formed by combining suitable amounts of (a) a polyisocyanate component and (b) an effective coating-forming amount of the asymmetric polyaspartic ester mixture. A coating is made from such a coating composition by (a) coating a substrate with a coating composition including effective coating-forming amounts of (i) a polyisocyanate component, and (ii) the asymmetric polyaspartic ester mixture. The polyisocyanate component and the asymmetric polyaspartic ester component are mixed in a ratio that is generally at least 0.9:1.1, preferably about 1:1 eq:eq, preferably from about 0.9:1.0 eq:eq to 1.5:1.0 and more preferably from about 0.9:1.0 eq:eq to 1.1:1 eq:eq. After the coating compositions have been applied to a suitable substrate, the compositions are hardened by curing at a suitable temperature, e.g., from about 30° C. to 150° C. In one embodiment, the polyisocyanate component and the effective coating-forming amounts of the asymmetric polyaspartic ester mixture also reacts with a polyol. Suitable polyols include polyols, e.g., polyethers such as those in U.S. Pat. No. 5,126,170, incorporated herein by reference in its entirety.

The coating can be made on substrates such as, cement, asphalt, metal, glass, and wood. The coatings are particularly useful in applications such as spray elastomer, heavy duty maintenance, product finishing, automotive, and flooring applications.

The invention will now be described in the following illustrative examples. All references to percentages are by weight unless otherwise indicated.

EXAMPLES

Example 1

In this example, an asymmetric polyaspartic ester mixture of the invention was made in accordance with the following procedure. A three-neck, round-bottom flask was fitted with stirrer, thermometer, nitrogen inlet, addition funnel and heater. One equivalent of diamine was added to the reactor. One equivalent of a 4:1 eq:eq mixture of dimethyl maleate and diethyl maleate was added through the addition funnel. The reaction was exothermic, and cooling was applied to maintain a temperature below 80° C. After addition of the maleate composition was complete, the mixture was heated at 60 to 80° C. for an additional 8 to 24 hours. The resin was then stored under ambient laboratory conditions until the reaction was complete. After nineteen days the unsaturation number was 0.8, indicating 98.5% of the reaction had completed. No crystals formed.

Comparative Example A

In this example, the procedure of Example 1 was repeated except that 290 g (5.0 eq) hexanediamine was placed in the reactor at 40° C. to melt the amine. 720.6 g (5.0 eq) dimethyl maleate was added over a one hour period. The reaction exothermed to 60° C. The reaction was heated at 60° C. for nine hours when needle-like crystals began to grow. After three days the unsaturation number was 88.71 given in terms of mg I per g maleic acid, indicating 85% reaction. The crystals were analyzed by GC, which indicated a composition of dimethyl fumarate.

Example 2

The procedure of Example 1 was repeated with the following exceptions. Hydrogenated diphenylmethane 4', 4'-diamine ($H_{12}$MDA) was used instead of hexamethylene diamine. An 0.8:0.2 eq:eq mixture of dimethyl maleate and diethyl maleate was used. After four days, the unsaturation number was 3.6, indicating 96.1% of the reaction had completed. No crystals formed.

Comparative Example B

The procedure of Example 2 was repeated except that 105 g (1.0 eq) of the $H_{12}$MDA was placed in the reactor at 25° C. 144.1 g (1.0 eq) dimethyl maleate was added over a one hour period while the reactor was held at 25° C. The reaction was heated at 60° C. for five hours. The reaction mixture was cooled to room temperature. The next morning the flask was full of dimethyl fumarate crystals.

Example 3

The procedure of Example 1 was repeated except that 119 g (1.0 eq) o,o'-Dimethyl$H_{12}$MDA (commercially known as Laromin C-260) was placed in the reactor at 25° C. 144.1 g (1.0 eq) of a 0.4:0.6 eq:eq mixture of dimethyl maleate and diethyl maleate was added over a one hour period while the reactor was held at 25° C. The reaction was heated at 60° C. for five hours. The reaction mixture was cooled to room temperature. After three days no crystals had formed.

Example 4

The procedure of Example 3 was repeated except that an 0.2:0.8 eq:eq mixture of dimethyl maleate and diethyl maleate was used. After four days the unsaturation number was 11.5, indicating 71.8% reaction. After three days no crystals formed.

Comparative Example C

The procedure of Example 3 was repeated except that 144.1 g (1.0 eq) dimethyl maleate was added over a one hour period while the reactor was held at 25° C. The reaction was heated at 60° C. for five hours. The reaction mixture was cooled to room temperature. The next morning the flask was full of dimethyl fumarate crystals.

Comparative Example D

The procedure of Example 3 was repeated except that an 0.8:0.2 eq:eq mixture of dimethyl maleate and diethyl maleate was used. After three days, the flask was full of dimethyl fumarate crystals.

Comparative Example E

The procedure of Example 3 was repeated except that a 0.6:0.4 eq:eq mixture of dimethyl maleate and diethyl maleate was used. After three days, the bottom of the flask had a layer of dimethyl fumarate crystals.

Comparative Example F

Example G of U.S. Pat. No. 5,126,170 was repeated and submitted to the analytical department for GC analysis. 119 g (1.0 eq) of the 3,3'-dimethyl-4,4'-diaminodicyclohexylmethane (available from BASF as Laromin C 260) and 263 g methanol were placed in a three-neck, round-bottom flask fitted with stirrer, .thermometer, nitrogen inlet, addition funnel and heater. The solution was heated to 60° C. 144.1 g (1.0 eq) dimethyl maleate was added dropwise over a one hour period while the reactor was held at 60° C. The reaction was heated at 60° C. for sixteen hours. The solvent was stripped from the reaction mixture under vacuum at 6° C. A small amount of dimethyl maleate crystals were recovered from the flask and were identified as such by GC. The unsaturation number of 1.84 mg maleic acid per g resin indicated that the Michael Addition Reaction was 96% complete. The viscosity was 2600 mPa.s. The amine number was 206 (theory was 192). Gas chromatographic (GC) analysis showed that considerable alcoholysis of the ethyl ester had occurred. The product consisted of random mixed methyl and ethyl esters.

Discussion of Comparative Example G

The GC analysis showed a mixture of methyl and ethyl esters of the polyaspartic esters. If it can be assumed that the high amine number is attributable to the alcoholysis to give a lower molecular weight resin, the amine number can be used to estimate the amount of alcohol exchange. The theoretical equivalent weight of the Laromine diethyl aspartate is 291. The actual equivalent weight, as calculated from the actual amine number, was 272. This means that there was a loss of mass of 19 or ~1.3 equivalents methylene. This means that one equivalent of aspartate ester product has ~0.32 ethyl ester groups and ~0.68 methyl ester groups. The difficulty with this process is the lack of control that the manufacturer has on the alcoholysis reaction. If the reaction is heated less, there will be less exchange; if heated more, more exchange. This leads to an inconsistent process.

Moreover, the product resulting from the ester alcoholysis differs from one where a mixture of dimethyl and diethyl esters is used. In the former case the product will consist of random mixtures of aspartate with dimethyl esters, diethyl esters and methyl ethyl esters. There is probably very little diethyl ester in the product based on the statistical distribution. Since there was ester alcoholysis, some amount of dimethyl fumarate would be made. Even though both ethyl and methyl aspartates were present in the product, this process did not prevent dimethyl fumarate precipitate as is taught by the present invention.

Comparative Example H

Comparative Example 1 was repeated except that dimethyl maleate was used in place of the diethyl maleate. In this case, much more dimethyl fumarate crystals were seen in the product. The use of methanol did not prevent formation of dimethyl fumurate.

Example 5

The resin of Example 2 was mixed with Desmodur N-3300 at an NCO to NH ratio of 1.0. The film was cast on a steel panel with a Byrd Applicator at 3 mil wet film thickness. The coating dried to a smooth and glossy film.

Comparative Example I

The unfiltered resin of Comparative Example 2 was mixed with Desmodur N-3300 at an NCO to NH ratio of 1.0. The film was cast on a steel panel with a Byrd Applicator at 3 mil wet film thickness. The coating dried to a film which exhibited many defects due to the presence of the dimethyl fumurate crystals protruding from the film.

Although the invention has been described in detail in the foregoing for the purpose of illustration, it is to be understood that such detail is solely for illustrative purposes and that variations can be made therein by those skilled in the art without departing from the spirit and scope of the invention.

What is claimed is:
1. A method for making a polyaspartic ester mixture which comprises reacting
   a) a mixture of
      i) a first ester component comprising a member selected from the group consisting of dimethyl maleate and methyl fumarate and
      ii) a second ester component comprising a member selected from the group consisting of esters of maleic acid substituted with alkyl groups having at least two carbon atoms and esters of fumaric esters substituted with alkyl groups having at least two carbon atoms, with (b) an amine component comprising a member selected from the group consisting of difunctional, trifunctional and tetrafunctional amines, wherein component ii) is present in an amount sufficient to prevent the formation of a reaction-stopping crude mixture containing dimethyl fumarate crystals and the reaction carried in the absence of an organic solvent or in the presence of less than 5% of an organic solvent, based on the total weight of the solution.

2. The method of claim 1 wherein amine b) comprises of cyclic amine containing a substituted functional group adjacent to a cyclically-bound amino group and wherein the equivalent ratio of component i) to component ii) is from less than 5:5 to more than 0:10.

3. The method of claim 1 wherein amine b) comprises an acyclic amine or a cyclic amine with or without a substituted group that is not adjacent to a cyclically-bound amino group, and wherein the equivalent ratio of component i) to component ii) is from less than 9:1 to more than 0:10.

4. The method of claim 1 wherein amine b) comprises a tetrafunctional amine.

5. The method of claim 1 which comprises reacting components a) and b) in the absence of an organic solvent.

6. The method of claim 1 wherein amine b) comprises a difunctional amine and the polyaspartic ester mixture contains a polyaspartic ester having the formula:

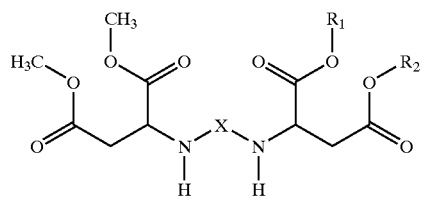

wherein X is a hydrocarbon group obtained by the removal of amino groups from a amine corresponding to the formula, $X-(NH_2)_n$, $R_1$ and $R_2$ are the same or different and represent an alkyl group having at least two carbon atoms and n is 2.

7. The method of claim 1 wherein amine b) comprises a trifunctional amine and the polyaspartic ester mixture comprises a polyaspartic ester having one of the following formulae:

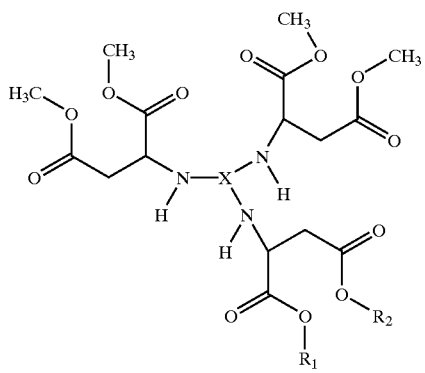

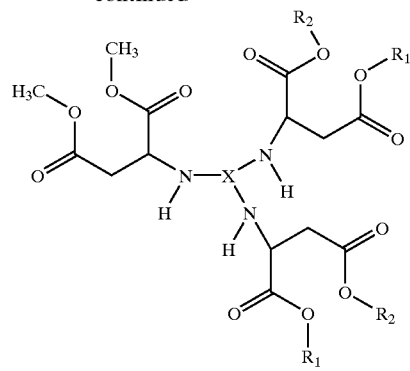

wherein X is a hydrocarbon group obtained by the removal of amino groups from an amine corresponding to the formula $X-(NH_2)_n$, $R_1$ and $R_2$ are the same or different and represent an alkyl group having at least two carbon atoms and n is 3.

8. The method of claim 1 wherein component ii) comprises a member selected from the group consisting of diethyl maleate and diethyl fumarate.

9. The method of claim 1 wherein amine b) comprises a cyclic amine containing a substituted functional group adjacent to a cyclically-bound amino group and wherein the equivalent ratio of component i) to component ii) is from 4.5:5.5 to 1:9.

10. The method of claim 1 wherein amine b) comprises an acyclic amine or a cyclic amine with or without a substituted group that is not adjacent to a cyclically-bound amino group, and wherein the equivalent ratio of component i) to component ii) is from 8.5:1.5 to 1:9.

11. The method of claim 2 which comprises reacting components a) and b) in the absence of an organic solvent.

12. The method of claim 3 which comprises reacting components a) and b) in the absence of an organic solvent.

13. The method of claim 6 which comprises reacting components a) and b) in the absence of an organic solvent.

14. The method of claim 8 which comprises reacting components a) and b) in the absence of an organic solvent.

15. The method of claim 9 which comprises reacting components a) and b) in the absence of an organic solvent.

16. The method of claim 10 which comprises reacting components a) and b) in the absence of an organic solvent.

17. An asymmetric polyaspartic ester mixture comprising the reaction product of a) a mixture of
i) a first ester component comprising a member selected from the group consisting of dimethyl maleate and dimethyl fumarate and
ii) a second ester component comprising a member selected from the group consisting of a dialkyl maleate and a dialkyl fumarate wherein the alkyl groups have at least two carbon atoms; with b) an amine component comprising a member selected from the group consisting of difunctional, trifunctional and tetrafunctional amines, wherein component ii) is present in an amount sufficient to prevent the formation of a reaction-stopping crude mixture containing dimethyl fumarate crystals.

18. The asymmetric polyaspartic ester mixture of claim 17 wherein amine b) comprises a cyclic amine containing a substituted functional group adjacent to a cyclically-bound amino group and wherein the equivalent ratio of component i) to component ii) is from less than 5:5 to more than 0:10.

19. The asymmetric polyaspartic ester mixture of claim 17 wherein amine b) comprises an acyclic amine or a cyclic amine with or without a substituted group that is not adjacent to a cyclically-bound amino group, and wherein the equivalent ratio of copmponent i) to component ii) is from less than 9:1 to more than 0:10.

20. The asymmetric polyaspartic ester mixture of claim 17 wherein amine b) comprises a tetrafunctional amine.

21. The asymmetric polyaspartic ester mixture of claim 17 wherein the asymmetric polyaspartic ester mixture contains less than 10% by weight, based on the weight of the solution, of an organic solvent.

22. The asymmetric polyaspartic ester mixture of claim 17 wherein amine b) comprises a difunctional amine and the asymmetric polyaspartic ester mixture contains a polyaspartic ester having the formula:

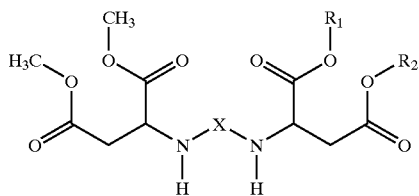

wherein X is a hydrocarbon group obtained by the removal of amino groups from a amine corresponding to the formula, $X-(NH_2)_n$, $R_1$ and $R_2$ are the same or different and represent an alkyl group having at least two carbon atoms and n is 2.

23. The asymmetric polyaspartic ester mixture of claim 17 wherein amine b) comprises a trifunctional amine and the polyaspartic ester mixture comprises a polyaspartic ester having one of the following formulae:

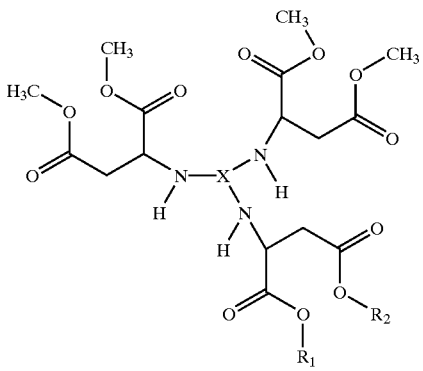

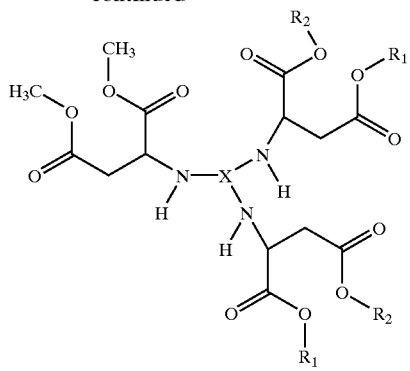

wherein X is a hydrocarbon group obtained by the removal of amino groups from an amine corresponding to the formula $X-(NH_2)_n$, $R_1$ and $R_2$ are the same or different and represent an alkyl group having at least two carbon atoms and n is 3.

24. The asymmetric polyaspartic ester mixture of claim 17 wherein component ii) comprises diethyl maleate or diethyl fumarate.

25. The asymmetric polyaspartic ester mixture of claim 17 wherein amine b) comprises a cyclic amine containing a substituted functional group adjacent to a cyclically-bound amino group and wherein the equivalent ratio of component i) to component ii) is from 4.5:5.5 to 1:9.

26. The asymmetric polyaspartic ester mixture of claim 17 wherein amine b) comprises an acyclic amine or a cyclic amine with or without a substituted group that is not adjacent to a cyclically-bound amino group, and wherein the equivalent ratio of component i) to component ii) is from 8.5:1.5 to 1:9.

* * * * *